(12) United States Patent
Reiner

(10) Patent No.: US 7,532,942 B2
(45) Date of Patent: May 12, 2009

(54) METHOD AND APPARATUS FOR GENERATING A TECHNOLOGIST QUALITY ASSURANCE SCORECARD

(76) Inventor: Bruce Reiner, 6 Greenleaf La., Seaford, DE (US) 19973

( * ) Notice: Subject to any disclaimer, the term of this patent is extended or adjusted under 35 U.S.C. 154(b) by 0 days.

(21) Appl. No.: 11/699,348

(22) Filed: Jan. 30, 2007

(65) Prior Publication Data

US 2007/0237308 A1    Oct. 11, 2007

Related U.S. Application Data

(60) Provisional application No. 60/762,859, filed on Jan. 30, 2006, provisional application No. 60/763,353, filed on Jan. 31, 2006, provisional application No. 60/763,357, filed on Jan. 31, 2006, provisional application No. 60/771,482, filed on Feb. 9, 2006, provisional application No. 60/771,484, filed on Feb. 9, 2006.

(51) Int. Cl.
*G06F 17/00* (2006.01)
*G06F 15/00* (2006.01)

(52) U.S. Cl. ............................ 700/90; 378/58; 378/62; 378/207; 382/132; 250/252.1

(58) Field of Classification Search ............. 700/90–93; 382/132; 378/207, 58, 62; 250/252.1
See application file for complete search history.

(56) References Cited

U.S. PATENT DOCUMENTS

| | | | | |
|---|---|---|---|---|
| 5,901,240 | A * | 5/1999 | Luo et al. | 382/132 |
| 5,903,660 | A * | 5/1999 | Huang et al. | 382/132 |
| 6,058,322 | A * | 5/2000 | Nishikawa et al. | 600/408 |
| 6,212,291 | B1 * | 4/2001 | Wang et al. | 382/132 |
| 6,345,114 | B1 * | 2/2002 | Mackie et al. | 382/132 |
| 6,502,985 | B1 * | 1/2003 | Garland et al. | 378/207 |
| 6,516,324 | B1 * | 2/2003 | Jones et al. | 707/104.1 |
| 6,763,128 | B1 * | 7/2004 | Rogers et al. | 382/130 |
| 6,950,492 | B2 * | 9/2005 | Besson | 378/5 |
| 6,950,493 | B2 * | 9/2005 | Besson | 378/16 |
| 7,116,749 | B2 * | 10/2006 | Besson | 378/16 |
| 7,142,633 | B2 * | 11/2006 | Eberhard et al. | 378/62 |
| 7,289,654 | B2 * | 10/2007 | Muller et al. | 382/132 |

(Continued)

OTHER PUBLICATIONS

"Radiation Therapy Oncology Group" RTOG 95-02. Phase IB Study of Radiosurgery and Etanidazole for the treatment of recurrent primary brain tumors or CNS metastases. Revisions 1-4, Mar. 7, 1997.*

(Continued)

*Primary Examiner*—Michael D Masinick
(74) *Attorney, Agent, or Firm*—Jean C. Edwards, Esq.; Akerman Senterfitt

(57) ABSTRACT

The present invention provides a quality assurance system and method that generates a quality assurance (QA) scorecard for technologists that use digital devices in a radiological-based medical imaging study. According to one embodiment, client computers, servers, imaging devices, databases, and/or other components may be coupled to provided a unified data collection system. According to one embodiment, systems and methods are provided that analyze various parameters that are derived from the unified data collection system to calculate a QA score for the technologist. The QA score provides a combined subjective and objective feedback system that includes performance evaluations from other users, including radiologists, clinicians and patients. According to one embodiment, the feedback may be provided in real-time.

15 Claims, 4 Drawing Sheets

U.S. PATENT DOCUMENTS

| | | | | |
|---|---|---|---|---|
| 2002/0010684 A1* | 1/2002 | Moskowitz | .................. | 705/75 |
| 2003/0212580 A1* | 11/2003 | Shen | ............................ | 705/2 |
| 2004/0202359 A1* | 10/2004 | Muller et al. | ............... | 382/131 |
| 2004/0252870 A1* | 12/2004 | Reeves et al. | ............... | 382/128 |
| 2005/0182657 A1* | 8/2005 | Abraham-Fuchs et al. | ..... | 705/2 |
| 2005/0203775 A1 | 9/2005 | Chesbrough | | |
| 2005/0238140 A1* | 10/2005 | Hardesty | ................... | 378/110 |
| 2006/0259282 A1* | 11/2006 | Failla et al. | .................... | 703/2 |

OTHER PUBLICATIONS

"Artifacts and misadventures in digital radiography", Willis et al, Applied Radiology, Jan. 2004.*

"Practical guidelines for radiographers to improve computed radiograph image quality", Pongnapang, Biomedical Imaging and Intervention Journal, Oct. 2005.*

"Quality assurance programs for diagnostic radiology facilities", Columbia University Medical Center, http://rso.cumc.columbia.edu/qaprog.htm.*

* cited by examiner

METHOD AND APPARATUS FOR GENERATING A TECHNOLOGIST QUALITY ASSURANCE SCORECARD

CROSS-REFERENCE TO RELATED APPLICATIONS

This application claims priority from U.S. Provisional Patent Application No. 60/762,859, dated Jan. 30, 2006, U.S. Provisional Patent Application No. 60/763,353, dated Jan. 31, 2006, U.S. Provisional Patent Application No. 60/763,357, dated Jan. 31, 2006, U.S. Provisional Patent Application No. 60/771,482, dated Feb. 9, 2006, U.S. Provisional Patent Application No. 60/771,484, dated Feb. 9, 2006, the contents of which are herein incorporated by reference in their entirety.

This application is related to the following concurrently filed commonly owned U.S. patent applications entitled, "Method And Apparatus For Generating A Patient Quality Assurance Scorecard" Ser. No. 11/699,349 filed Jan. 30, 2007); "Method And Apparatus For Generating An Administrative Quality Assurance Scorecard" Ser. No. 11/699,350 filed Jan. 30, 2007); "Method And Apparatus For Generating A Radiologist Quality Assurance Scorecard" Ser. No. 11/699,344 filed Jan. 30, 2007); and "Method And Apparatus For Generating A Clinician Quality Assurance Scorecard" Ser. No. 11/699,351 filed Jan. 30, 2007), the contents of all of which are herein incorporated by reference in their entirety.

BACKGROUND OF THE INVENTION

1. Field of the Invention

The present invention relates to a quality assurance (QA) system and method that quantitatively rates users that perform and/or participate in medical procedures, particularly in the area of radiology. The present invention relates to systems, methods and computer-based software programs that analyze data and generate QA scorecards for technologists. In the process of doing so, a number of objective data are collected for real-time and future analysis, thereby providing objective feedback to technologists for continuing quality improvement. In the end, the invention is intended to improve patient safety and overall clinical outcomes.

2. Description of the Related Art

The first and foremost priority for any QA program is to improve quality of service. As QA programs are implemented in the medical field, the ultimate goal is to improve patient care. To accomplish this goal, products and/or services should offer procedures for increasing accountability and improving feedback among users that participate in a medical study. This ultimately will enhance patient diagnosis and/or treatment, which leads to objective improvements in overall health outcomes.

Medical imaging has undergone a transition from film-based imaging technologies to digital imaging technologies. Digital imaging technologies provide digital processing capabilities, such as image capture, image archive, image transfer, and image display that may be shared among users to the medical study. Digital imaging technologies further allow data that is associated with the digital processing operations to be captured and combined with the underlying digital imaging processing operations.

Accordingly, a need exists to leverage digital imaging technologies to increase accountability and improve feedback among users that participate in a medical study.

SUMMARY OF THE INVENTION

The present invention relates to systems, methods and computer-based software programs that provide a QA scorecard for users that participate in a radiology imaging study. The QA scorecard provides the framework for developing a comprehensive medical imaging QA program that defines objective benchmarks. One of ordinary skill in the art will readily recognize that this invention may be applied to other medical disciplines, as well as to non-medical disciplines.

According to one embodiment, the invention is directed to radiological-based medical studies using digital imaging technologies. The medical studies are performed by many users that perform discrete tasks in an imaging study workflow sequence. According to one embodiment of the invention, users include clinicians, radiologists, technologists, administrators and patients, among other users. A typical workflow sequence includes imaging exam ordering, imaging exam scheduling, imaging exam acquisition, imaging exam processing, imaging exam archiving, imaging exam distribution, imaging exam display, imaging exam navigation, imaging exam interpretation, imaging exam reporting, communication and billing, among other sequences.

According to one embodiment of the invention, client computers, one or more servers, the imaging devices, one or more databases, and/or other components may be coupled via a wired media, a wireless media, or a combination of the foregoing to provided a unified data collection system.

According to one embodiment of the invention, the client computers may include any number of different types of client terminal devices, such as personal computers, laptops, smart terminals, personal digital assistants (PDAs), cell phones, portable processing devices that combine the functionality of one or more of the foregoing or other client terminal devices.

According to one embodiment, the client computer may include client computer agent modules that gather client computer monitoring data based on user actions that are performed. According to another embodiment of the invention, user action data may include accessing digital images, reviewing digital images, manipulating digital images, marking digital images, storing digital images, forwarding digital images, adjusting exposure parameters on digital imaging devices, generating a report, generating a textual report, dictating a report, entering information, conducting continuing medical education (CME) triggered by performing the medical examination, and/or performing other user actions.

According to one embodiment, the client computer may include client computer agent modules that gather client computer monitoring data based on computer actions that are performed. According to one embodiment of the invention, the client computer agent modules also may gather client computer specification data, such as IP address data, processing speed data, and other client computer specification data. According to one embodiment of the invention, the client monitoring data and/or client computer specification data may be provided in real-time. According to another embodiment of the invention, the client monitoring data and/or client computer specification data may be employed to calculate user QA metrics.

According to one embodiment, the metrics module analyzes data that is associated with a defined list of quality assurance (QA) benchmarks to objectively evaluate technologists, quantify a relative success of image acquisition and image processing and provide educational (data-driven) feedback in order to optimize technologist performance, among other benefits. The QA metrics may be tied to economic incentives, such as a pay for performance (P4P) systems, to create financial rewards for those technologists that provide high levels of quality-oriented service deliverables.

According to one embodiment, a quantifiable list of predefined technologist performance parameters which are defined by the computer program may be used to measure overall performance of the technologist such as education, training, and certification; image quality scores; patient safety; dose reduction; data input, documentation, and verification; adherence to imaging and institutional protocols; trending analysis from QA database; image processing, among other parameters by the program 110.

According to one embodiment of the invention, the imaging devices may include any number of different types of imaging devices, such as magnetic resonance imaging (MRI) devices, computer tomograph (CT) imaging devices, angiograph imaging device, ultrasound imaging devices or other imaging devices.

According to one embodiment of the invention, the imaging devices may include, or be modified to include, imaging device agent modules. The imaging device agent modules may operate to provide data gathering and data exchange functionality. According to one embodiment, the invention may enable monitoring of actions that are performed on the imaging devices.

According to one embodiment of the invention, the imaging device agent modules may associate imaging device-identifying-information with actions that are performed on the imaging devices. According to one embodiment of the invention, data monitoring features may be employed to generate imaging device audit logs. According to one embodiment of the invention, image device audit logs may be produced to reconstruct actions, such as user actions, imaging device actions, and other actions that are performed on (or by) the imaging devices.

According to one embodiment of the invention, databases or information sources include a Hospital Information System (HIS) 10, a Radiology Information System (RIS) 20, a Picture Archiving and Communication System (PACS) 30, an Electronic Medical Record (EMR), a patient specific imaging datasheet and/or other information sources.

According to one embodiment of the invention, the server may include a merging module that receives data from all devices that are networked to the server, including the client computers, the imaging devices, and/or databases or information sources. According to one embodiment of the invention, the received data may include at least client computer audit log data and/or image device audit log data. According to one embodiment, the merging module merges data that is captured during a medical examination, including user action data, client computer action data, imaging device action, data, and other data.

According to one embodiment of the invention, the data that is collected during the imaging study may analyzed by a metrics module that performs prospective and retrospective trending analysis. The prospective and retrospective trending analysis enables automatic detection of immediate and recurrent problems, as they relate to equipment, personnel, data input, and overall workflow. The result of this automated technical QA analysis is that an automated and normalized analysis may be performed that minimizes subjectivity and human bias, among providing other benefits.

According to one embodiment of the invention, the metrics module may automatically tally and record QA scores. The QA scores may be cross-referenced by the computer program to a number of independent variables including a technologist identifier, imaging modality, exam type, patient demographics, patient characteristics, patient body habitus, exposure parameters, image processing, exam location, equipment, day/time of exam for trending analysis, radiologist identification, referring clinician, clinical indication, among other variables.

According to one embodiment of the invention, a standard tag may be created by the program within the various informational sources to identify individual QA data parameters. The communication module may extract the parameters from the CPOE entries to calculate metrics and generate a QA score for the clinician.

According to one embodiment of the invention, the QA metrics module may analyze various parameters to calculate a QA score for the technologist. According to one embodiment, the time-stamped data is a component part of objective data analysis. Imaging departments may utilize a program to record individual time-stamped data throughout the course of the imaging cycle, from the time an imaging exam is electronically ordered to the time the imaging report issued and reviewed. This is time-stamped data may be recorded into a QA database for subsequent analysis.

According to one embodiment, in order to optimize safety concerns and record/track cumulative data, the QA scorecard program provides patient safety data at any location where the patient is seeking and/or receiving medical imaging services. By storing the QA Scorecard data within a universal EMR, this data is made accessible to appropriate healthcare providers at any location.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
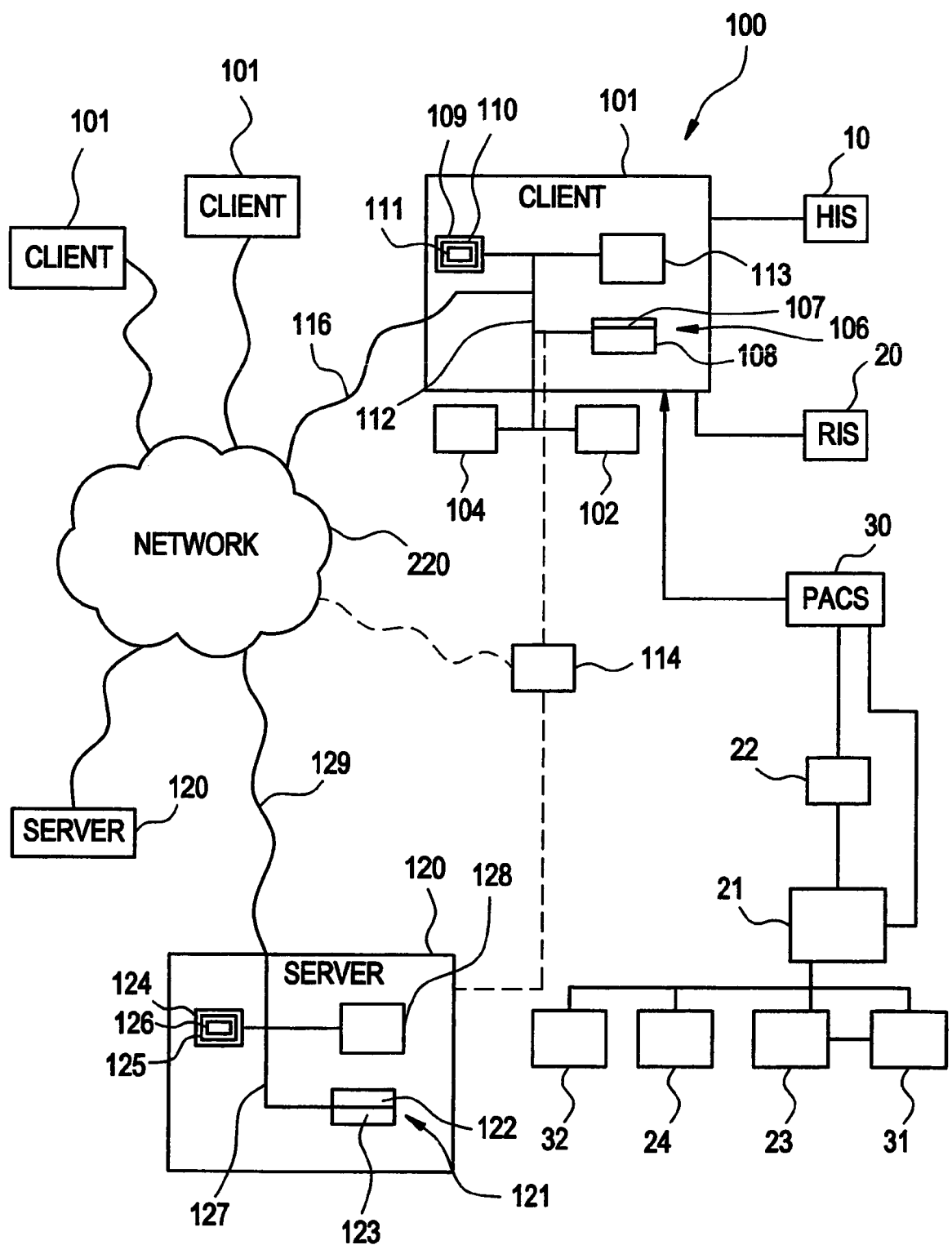
FIG. 1 illustrates a schematic diagram of a quality assurance scorecard system for radiology, according to one embodiment of the present invention.

The present invention relates to systems, methods, and computer-based software programs for generating quality assurance (QA) metrics, or scorecards, for technologists that participate in radiological-based medical studies.

Radiological-based medical studies of the present invention are conducted using digital imaging technologies. The medical studies are performed by many users that perform discrete tasks in an imaging study workflow sequence. Typically, the workflow sequence is initiated by a clinician, such as a family practice physician, that examines a patient and orders an imaging examination. The clinician's staff contacts an imaging center and schedules the imaging examination. At the imaging center, a technologist operates one or more imaging devices to acquire patient images. In some cases, the number of patient images taken may total several hundred or several thousand images. During the image acquisition operation, the technologist may process the images, including applying algorithms to the raw imaging data in order to enhance selected image features, reconstructing the raw image data in different ways to optimize imaging views, and/or performing other image processing. Upon completion of the imaging examination, the patient may be discharged from the imaging facility and the images may be locally stored. Generally, imaging administrators periodically obtain the images from the local storage devices and archive the images in a database, such as a Picture Archival Retrieval System (PACS) and/or other imaging databases. The images may be archived and retrieved based on selected criteria, including patient name, patient reference number, patient identifier, physician identifier, and/or other selected criteria.

After the images are archived, the images may be distributed to one or more specialists, such as a radiologist. Alternatively, a message may be communicated to one or more specialists advising the specialists that the images are available and providing instructions for accessing the archived images from the PACS or other imaging databases. The radiologist may access the PACS or other imaging databases and may perform image display and image navigation functions. The radiologist interprets the images and may access decision support tools or other interpretation tools during the image interpretation process. Following the image interpretation, the radiologist may generate a report and/or otherwise communicate the image study results to the referring clinician, among others. Upon completion of the imaging process, the radiologist, an administrator, and/or other service provider may perform billing operations. Additionally, the administrator may be tasked with defining the lines of responsibility for the participants of the imaging exam and for developing a comprehensive program that ensures appropriate levels of quality, while balancing economics, service deliverables and productivity. One of ordinary skill in the art will readily appreciate that the imaging study workflow sequence may include other operations.

According to one embodiment of the invention illustrated in FIG. 1, medical (radiological) applications may be implemented using the QA scorecard system 100. The QA scorecard system 100 is designed to interface with existing information systems such as a Hospital Information System (HIS) 10, a Radiology Information System (RIS) 20, a radiographic device 21, and/or other information systems that may access a computed radiography (CR) cassette or direct radiography (DR) system, a CR/DR plate reader 22, a Picture Archiving and Communication System (PACS) 30, and/or other systems. The QA scorecard system 100 may be designed to conform with the relevant standards, such as the Digital Imaging and Communications in Medicine (DICOM) standard, DICOM Structured Reporting (SR) standard, and/or the Radiological Society of North America's Integrating the Healthcare Enterprise (IHE) initiative, among other standards.

According to one embodiment, bi-directional communication between the QA scorecard system 100 of the present invention and the information systems, such as the HIS 10, RIS 20, radiographic device 21, CR/DR plate reader 22, and PACS 30, etc., may be enabled to allow the QA scorecard system 100 to retrieve and/or provide information from/to these systems. According to one embodiment of the invention, bi-directional communication between the QA scorecard system 100 of the present invention and the information systems allows the QA scorecard system 100 to update information that is stored on the information systems. According to one embodiment of the invention, bi-directional communication between the QA scorecard system 100 of the present invention and the information systems allows the QA scorecard system 100 to generate desired reports and/or other information.

The QA scorecard system 100 of the present invention includes a client computer 101, such as a personal computer (PC), which may or may not be interfaced or integrated with the PACS 30. The client computer 101 may include an imaging display device 102 that is capable of providing high resolution digital images in 2-D or 3-D, for example. According to one embodiment of the invention, the client computer 101 may be a mobile terminal if the image resolution is sufficiently high. Mobile terminals may include mobile computing devices, a mobile data organizer (PDA), or other mobile terminals that are operated by the user accessing the program 110 remotely.

According to one embodiment of the invention, an input device 104 or other selection device, may be provided to select hot clickable icons, selection buttons, and/or other selectors that may be displayed in a user interface using a menu, a dialog box, a roll-down window, or other user interface. The user interface may be displayed on the client computer 101. According to one embodiment of the invention, users may input commands to a user interface through a programmable stylus, keyboard, mouse, speech processing device, laser pointer, touch screen, or other input device 104.

According to one embodiment of the invention, the input or other selection device 104 may be implemented by a dedicated piece of hardware or its functions may be executed by code instructions that are executed on the client processor 106. For example, the input or other selection device 104 may be implemented using the imaging display device 102 to display the selection window with a stylus or keyboard for entering a selection.

According to another embodiment of the invention, symbols and/or icons may be entered and/or selected using an input device 104, such as a multi-functional programmable stylus. The multi-functional programmable stylus may be used to draw symbols onto the image and may be used to accomplish other tasks that are intrinsic to the image display, navigation, interpretation, and reporting processes, as described in U.S. patent application Ser. No. 11/512,199 filed on Aug. 30, 2006, the entire contents of which are hereby incorporated by reference. The multi-functional programmable stylus may provide superior functionality compared to traditional computer keyboard or mouse input devices. According to one embodiment of the invention, the multi-functional programmable stylus also may provide superior functionality within the PACS and Electronic Medical Report (EMR).

According to one embodiment of the invention, the client computer 101 may include a processor 106 that provides client data processing. According to one embodiment of the invention, the processor 106 may include a central processing unit (CPU) 107, a parallel processor, an input/output (I/O) interface 108, a memory 109 with a program 110 having a data structure 111, and/or other components. According to one embodiment of the invention, the components all may be connected by a bus 112. Further, the client computer 101 may include the input device 104, the image display device 102, and one or more secondary storage devices 113. According to one embodiment of the invention, the bus 112 may be internal to the client computer 101 and may include an adapter that enables interfacing with a keyboard or other input device 104. Alternatively, the bus 112 may be located external to the client computer 101.

According to one embodiment of the invention, the image display device 102 may be a high resolution touch screen computer monitor. According to one embodiment of the invention, the image display device 102 may clearly, easily and accurately display images, such as x-rays, and/or other images. Alternatively, the image display device 102 may be implemented using other touch sensitive devices including tablet personal computers, pocket personal computers, plasma screens, among other touch sensitive devices. The touch sensitive devices may include a pressure sensitive screen that is responsive to input from the input device 104, such as a stylus, that may be used to write/draw directly onto the image display device 102.

According to another embodiment of the invention, high resolution goggles may be used as a graphical display to provide end users with the ability to review images. According to another embodiment of the invention, the high resolution goggles may provide graphical display without imposing physical constraints of an external computer.

According to another embodiment, the invention may be implemented by an application that resides on the client computer 101, wherein the client application may be written to run on existing computer operating systems. Users may interact with the application through a graphical user interface. The client application may be ported to other personal computer (PC) software, personal digital assistants (PDAs), cell phones, and/or any other digital device that includes a graphical user interface and appropriate storage capability.

According to one embodiment of the invention, the processor 106 may be internal or external to the client computer 101. According to one embodiment of the invention, the processor 106 may execute a program 110 that is configured to perform predetermined operations. According to one embodiment of the invention, the processor 106 may access the memory 109 in which may be stored at least one sequence of code instructions that may include the program 110 and the data structure 111 for performing predetermined operations. The memory 109 and the program 110 may be located within the client computer 101 or external thereto.

While the system of the present invention may be described as performing certain functions, one of ordinary skill in the art will readily understand that the program 110 may perform the function rather than the entity of the system itself.

According to one embodiment of the invention, the program 110 that runs the QA scorecard system 100 may include separate programs 110 having code that performs desired operations. According to one embodiment of the invention, the program 110 that runs the QA scorecard system 100 may include a plurality of modules that perform sub-operations of an operation, or may be part of a single module of a larger program 110 that provides the operation.

According to one embodiment of the invention, the processor 106 may be adapted to access and/or execute a plurality of programs 110 that correspond to a plurality of operations. Operations rendered by the program 110 may include, for example, supporting the user interface, providing communication capabilities, performing data mining functions, performing e-mail operations, and/or performing other operations.

According to one embodiment of the invention, the data structure 111 may include a plurality of entries. According to one embodiment of the invention, each entry may include at least a first storage area, or header, that stores the databases or libraries of the image files, for example.

According to one embodiment of the invention, the storage device 113 may store at least one data file, such as image files, text files, data files, audio files, video files, among other file types. According to one embodiment of the invention, the data storage device 113 may include a database, such as a centralized database and/or a distributed database that are connected via a network. According to one embodiment of the invention, the databases may be computer searchable databases. According to one embodiment of the invention, the databases may be relational databases. The data storage device 113 may be coupled to the server 120 and/or the client computer 101, either directly or indirectly through a communication network, such as a LAN, WAN, and/or other networks. The data storage device 113 may be an internal storage device. According to one embodiment of the invention, QA scorecard system 100 may include an external storage device 114. According to one embodiment of the invention, data may be received via a network and directly processed.

According to one embodiment of the invention, the client computer 101 may be coupled to other client computers 101 or servers 120. According to one embodiment of the invention, the client computer 101 may access administration systems, billing systems and/or other systems, via a communication link 116. According to one embodiment of the invention, the communication link 116 may include a wired and/or wireless communication link, a switched circuit communication link, or may include a network of data processing devices such as a LAN, WAN, the Internet, or combinations thereof. According to one embodiment of the invention, the communication link 116 may couple e-mail systems, fax systems, telephone systems, wireless communications systems such as pagers and cell phones, wireless PDA's and other communication systems.

According to one embodiment of the invention, the communication link 116 may be an adapter unit that is capable of executing various communication protocols in order to establish and maintain communication with the server 120, for example. According to one embodiment of the invention, the communication link 116 may be implemented using a specialized piece of hardware or may be implemented using a general CPU that executes instructions from program 110. According to one embodiment of the invention, the communication link 116 may be at least partially included in the processor 106 that executes instructions from program 110.

According to one embodiment of the invention, if the server 120 is provided in a centralized environment, the server 120 may include a processor 121 having a CPU 122 or parallel processor, which may be a server data processing device and an I/O interface 123. Alternatively, a distributed CPU 122 may be provided that includes a plurality of individual processors 121, which may be located on one or more machines. According to one embodiment of the invention, the processor 121 may be a general data processing unit and may include a data processing unit with large resources (i.e., high processing capabilities and a large memory for storing large amounts of data).

According to one embodiment of the invention, the server 120 also may include a memory 124 having a program 125 that includes a data structure 126, wherein the memory 124 and the associated components all may be connected through bus 127. If the server 120 is implemented by a distributed system, the bus 127 or similar connection line may be implemented using external connections. The server processor 121 may have access to a storage device 128 for storing preferably large numbers of programs 110 for providing various operations to the users.

According to one embodiment of the invention, the data structure 126 may include a plurality of entries, wherein the entries include at least a first storage area that stores image files. Alternatively, the data structure 126 may include entries that are associated with other stored information as one of ordinary skill in the art would appreciate.

According to one embodiment of the invention, the server 120 may include a single unit or may include a distributed system having a plurality of servers 120 or data processing units. The server(s) 120 may be shared by multiple users in direct or indirect connection to each other. The server(s) 120 may be coupled to a communication link 129 that is preferably adapted to communicate with a plurality of client computers 101.

According to one embodiment, the present invention may be implemented using software applications that reside in a client and/or server environment. According to another embodiment, the present invention may be implemented using software applications that reside in a distributed system over a computerized network and across a number of client computer systems. Thus, in the present invention, a particular operation may be performed either at the client computer 101, the server 120, or both.

According to one embodiment of the invention, in a client-server environment, at least one client and at least one server are each coupled to a network 220, such as a Local Area Network (LAN), Wide Area Network (WAN), and/or the Internet, over a communication link 116, 129. Further, even though the systems corresponding to the HIS 10, the RIS 20, the radiographic device 21, the CR/DR reader 22, and the PACS 30 (if separate) are shown as directly coupled to the client computer 101, it is known that these systems may be indirectly coupled to the client over a LAN, WAN, the Internet, and/or other network via communication links. According to one embodiment of the invention, users may access the various information sources through secure and/or non-secure internet connectivity. Thus, operations consistent with the present invention may be carried out at the client computer 101, at the server 120, or both. The server 120, if used, may be accessible by the client computer 101 over the Internet, for example, using a browser application or other interface.

According to one embodiment of the invention, the client computer 101 may enable communications via a wireless service connection. The server 120 may include communications with network/security features, via a wireless server, which connects to, for example, voice recognition. According to one embodiment, user interfaces may be provided that support several interfaces including display screens, voice recognition systems, speakers, microphones, input buttons, and/or other interfaces. According to one embodiment of the invention, select functions may be implemented through the client computer 101 by positioning the input device 104 over selected icons. According to another embodiment of the invention, select functions may be implemented through the client computer 101 using a voice recognition system to enable hands-free operation. One of ordinary skill in the art will recognize that other user interfaces may be provided.

According to another embodiment of the invention, the client computer 101 may be a basic system and the server 120 may include all of the components that are necessary to support the software platform. Further, the present client-server system may be arranged such that the client computer 101 may operate independently of the server 120, but the server 120 may be optionally connected. In the former situation, additional modules may be connected to the client computer 101. In another embodiment consistent with the present invention, the client computer 101 and server 120 may be disposed in one system, rather being separated into two systems.

Although the above physical architecture has been described as client-side or server-side components, one of ordinary skill in the art will appreciate that the components of the physical architecture may be located in either client or server, or in a distributed environment.

Further, although the above-described features and processing operations may be realized by dedicated hardware, or may be realized as programs having code instructions that are executed on data processing units, it is further possible that parts of the above sequence of operations may be carried out in hardware, whereas other of the processing operations may be carried out using software.

The underlying technology allows for replication to various other sites. Each new site may maintain communication with its neighbors so that in the event of a catastrophic failure, one or more servers 120 may continue to keep the applications running, and allow the system to load-balance the application geographically as required.

Further, although aspects of one implementation of the invention are described as being stored in memory, one of ordinary skill in the art will appreciate that all or part of the invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems of the present invention may contain additional or different components.

Figure 2:
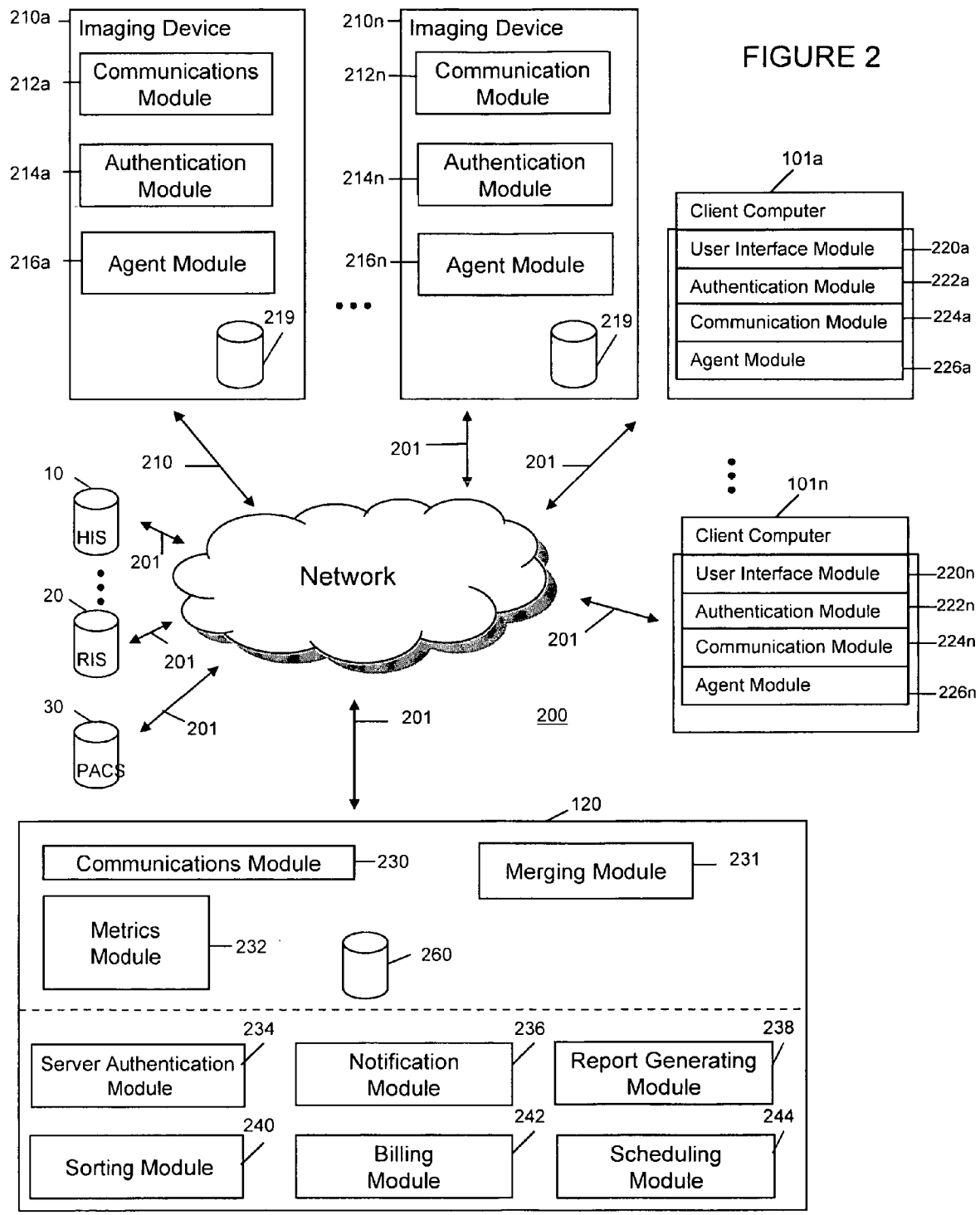
FIG. 2 illustrates a schematic diagram of a quality assurance scorecard system for radiology, according to another embodiment of the present invention.

FIG. 2 illustrates the QA scorecard system 100 for providing QA assessments of technologists that access a radiology system, according to one embodiment of the invention. According to one embodiment, the client computers 101a-101n (hereinafter client computers 101), one or more servers 120, the imaging devices 210a-210n (hereinafter imaging devices 210), one or more databases (HIS 10, RIS 20, PACS 30, etc.), and/or other components may be coupled via a wired media, a wireless media, or a combination of the foregoing. According to one embodiment of the invention, the client computers 101, the server 120, the imaging devices 210, and the databases may reside in one or more networks, such as an internet, an intranet, or a combination thereof.

According to one embodiment of the invention, the client computers 101 may include any number of different types of client terminal devices, such as personal computers, laptops, smart terminals, personal digital assistants (PDAs), cell phones, portable processing devices that combine the functionality of one or more of the foregoing or other client terminal devices.

According to another embodiment of the invention, the client computers 101 may include several components, including processors, RAM, a USB interface, a telephone interface, microphones, speakers, a stylus, a computer mouse, a wide area network interface, local area network interfaces, hard disk drives, wireless communication interfaces, DVD/CD readers/burners, a keyboard, a flat touch-screen display, a computer display, and/or other components. According to yet another embodiment of the invention, client computers 101 may include, or be modified to include, software that may operate to provide data gathering and data exchange functionality.

According to one embodiment of the invention, the client computers 101, the servers 120, and/or the imaging devices 210 may include several modules. The modular construction facilitates adding, deleting, updating and/or amending modules therein and/or features within modules. The client computer 101 may include various modules, including a user interface module 220, an authentication module 222, a communications module 224, an agent module 226, and/or other modules. The servers 120 may include various modules, including a server communication module 230, a merging module 231, a metrics module 232, a server authentication module 234, a notification module 236, a report generating module 238, a sorting module 240, a billing module 242, scheduling module 244 and/or other modules. The imaging devices 210 may include various modules, including a communications module 212, an authentication module 214, an agent module 216 and/or other modules, along with a local storage device 219. It should be readily understood that a greater or lesser number of modules might be used. One skilled in the art will readily appreciate that the invention may be implemented using individual modules, a single module that incorporates the features of two or more separately described modules, individual software programs, and/or a single software program.

According to one embodiment of the invention, the client computer 101 may communicate through a networking application. According to another embodiment, the user interface modules 220a-220n (hereinafter user interface modules 220) may support several interfaces including display screens, voice recognition systems, speakers, microphones, input buttons, and/or other interfaces. According to one embodiment of the invention, the user interface modules 220 may display the application on a user interface associated with the client computer 101. According to one embodiment of the invention, select functions may be implemented through the client computer 101 by positioning an indicator over selected icons and manipulating an input device 104, such as a stylus, a mouse, a keyboard, or other input devices.

With regard to user authentication, the authentication modules 222a-222n (hereinafter user authentication modules 222) may employ one of several different authentication schemes, as would be appreciated by those skilled in the art. According to one embodiment of the invention, the user authentication modules 222 may prompt users to input alphanumeric code or other identifying information. According to another embodiment of the invention, the user authentication modules 222 may prompt users to provide biometric information (i.e., a thumbprint through a fingerprint scanner) or other suitable identifying information. If the user is not identified, then the user may be invited to resubmit the requested identification information or to take other action.

According to one embodiment of the invention, the client computers 101 may include communication modules 224a-224n (hereinafter communication modules 224) for enabling the client computers 101 to communicate with systems, including other client computers, the servers 120, the imaging devices 210, the databases and/or other systems. The client computers 101 may communicate via communications media 201 such as, for example, any wired and/or wireless media. Communications between the client computers 101, the imaging devices 210, the servers 120, and the databases may occur substantially in real-time, when the devices are coupled to the network. According to one embodiment of the invention, the communications module 224 may communicate with the servers 120 to exchange data, wherein the data exchange may occur with or without user awareness of the data exchange.

According to an alternative embodiment of the invention, communications may be delayed for an amount of time if, for example, one or more client computers 101, the server 120, the imaging devices 210, and/or the databases are not coupled to the network. According to one embodiment of the invention, any requests that are submitted while devices are not coupled to the network may be stored and propagated from/to the offline client computer 101, the databases and/or the imaging devices 210 when the target devices are re-coupled to the network. One of ordinary skill in the art will appreciate that communications may be conducted in various ways and among various devices.

According to one embodiment of the invention, user authentication information and/or identification information may be forwarded to the servers 120 to perform various functions. According to another embodiment of the invention, the servers 120 may operate to coordinate communications between the applications that are associated with the client computers 101, the imaging devices 210, and/or the databases.

According to one embodiment of the invention, the client computers 101 may include, or be modified to include, client computer agent modules 226a-226n (hereinafter client computer agent modules 226). The client computer agent modules 226 may operate to provide data gathering and data exchange functionality. According to one embodiment, the invention may enable monitoring of actions that are performed on the client computers 101.

According to one embodiment of the invention, the client computer agent modules 226 may associate client computer identifying information with actions that are performed on the corresponding client computers 101. According to one embodiment of the invention, data monitoring features may be employed to generate client computer audit logs. According to one embodiment of the invention, client computer audit logs may be produced to reconstruct actions, such as user actions, computer actions, and/or other actions that are performed on (or by) the client computers 101.

According to one embodiment, the client computer agent modules 226 may gather client computer monitoring data based on user actions performed, such as user login information; data files and databases that are accessed; information that is requested, including patient names/identifiers, exam results; information that is retrieved; client computer access information, including user information, time of access, time of exit, etc.; the application(s) that are used; information that is obtained from the server 120, including time of access, patient identifiers, volume of data retrieved, etc.; information that is obtained from the imaging devices 210, including time of access, patient identifiers, volume of data retrieved, etc.; information that is processed at the client computer 101, including time stamp information; and other user action data. According to another embodiment of the invention, user action data may include accessing digital images, reviewing digital images, manipulating digital images, marking digital images, storing digital images, forwarding digital images, adjusting exposure parameters on digital imaging devices, generating a report, generating a textual report, dictating a report, entering information, conducting continuing medical education (CME) triggered by performing the medical examination, and/or performing other user actions.

According to one embodiment, the client computer agent modules 226 may gather client computer monitoring data based on computer actions performed, such as when data is exchanged; the type of input device used; whether reports are printed; when data is saved; an Internet Protocol (IP) address of devices that are communicated with; a location of data storage/retrieval; etc.; and/or other computer action data. According to one embodiment of the invention, the client computer agent modules 226 also may gather client computer specification data, such as IP address data, processing speed data, and other client computer specification data. According to one embodiment of the invention, the client monitoring data and/or client computer specification data may be provided in real-time. According to another embodiment of the invention, the client monitoring data and/or client computer specification data may be employed to calculate user QA metrics.

According to one embodiment of the invention, the server 120 may include a server authentication module 234 that receives authentication information that is entered into a corresponding client computer 101 via the authentication modules 222. The server authentication module 234 may compare the identifying information with existing records and operate as a gatekeeper to the QA scorecard system 100. If the user is determined to be a registered user, the authentication module 234 may attempt to authenticate the registered user by matching the entered authentication information with access information that exists on the servers 120. If the user is not authenticated, then the user may be invited to resubmit the requested identifying information or take other action. If the user is authenticated, then the servers 120 may perform other processing. For example, the client computers 101 may receive information from the servers 120 and/or from another authenticated client computers.

According to one embodiment of the invention, the imaging devices 210 may include any number of different types of imaging devices, such as magnetic resonance imaging (MRI) devices, computer tomograph (CT) imaging devices, angiograph imaging device, ultrasound imaging devices or other imaging devices. According to another embodiment of the invention, the imaging devices 210 may include several components such as processors, databases 219a-219n (hereinafter databases 219), RAM, a USB interface, a telephone interface, microphones, speakers, a stylus, a computer mouse, a wide area network interface, local area network interfaces, hard disk drives, wireless communication interfaces, a keyboard, a flat touch-screen display, a computer display, and/or other components.

According to one embodiment of the invention, the imaging devices 210 may include, or be modified to include, imaging device agent modules 216a-216n (hereinafter imaging device agent modules 216). The imaging device agent modules 216 may operate to provide data gathering and data exchange functionality. According to one embodiment, the invention may enable monitoring of actions that are performed on the imaging devices 210.

According to one embodiment of the invention, the imaging device agent modules 216 may associate imaging device identifying information with actions that are performed on the imaging devices 210. According to one embodiment of the invention, data monitoring features may be employed to generate imaging device audit logs. According to one embodiment of the invention, image device audit logs may be produced to reconstruct actions, such as user actions, imaging device actions, and other actions that are performed on (or by) the imaging devices 210.

According to one embodiment, the imaging device agent modules 216 may gather image device monitoring data based on user actions performed, such as user login information; imaging modalities; parameters that are selected to perform the imaging modalities, including motion information, positioning information, exposure information, artifact information, collimation information; number of times an imaging exam is performed; data files and databases that are accessed; information that is requested, including patient names/identifiers; information that is retrieved; imaging device access information, including user information, time of access, time of exit, etc.; information that is stored to the server 120, including time of storage, patient identifiers, volume of data stored, etc.; information that was obtained from the imaging devices 210, including time of access, patient identifiers, volume of data stored, etc.; information that was processed at the imaging device 210, including time stamp information; and other user action data.

According to one embodiment, the imaging device agent modules 216 may gather imaging device monitoring data based on imaging device actions performed, such as when data is exchanged; the type of input device used; whether reports are printed; when data was saved; an Internet Protocol (IP) address of devices that were communicated with; a location of data storage/retrieval; imaging device parameter adjustments; and other imaging device data. According to one embodiment of the invention, the imaging device agent modules 216 also may gather imaging device specification data, such as resolution data, IP address data, processing speed data, and other imaging device specification data. According to one embodiment of the invention, the imaging device monitoring data and/or imaging device specification data may be stored in database 219. According to one embodiment of the invention, the imaging device monitoring data and/or imaging device specification data of the program 110 may be provided in real-time. According to another embodiment of the invention, the imaging device monitoring data and/or imaging device specification of the program 110 may be employed to calculate user QA metrics. The inventor has previously submitted an application describing an apparatus for automating QA in medical imaging, as described in U.S. patent application Ser. No. 11/412,884 filed on Apr. 28, 2006, the entire contents of which are hereby incorporated by reference.

According to one embodiment of the invention, the server 120 may include a merging module 231 that receives data from all devices that are networked to the server 120, including the client computers 101, the imaging devices 210, and/or databases. According to one embodiment of the invention, the received data may include at least client computer audit log data and/or image device audit log data. The merging module 231 may locally store the received data in a storage device 260 and/or may store the received data in an external storage device. The merging module 231 merges data that is captured during a medical examination, including user action data, client computer action data, imaging device action data, and other data.

According to one embodiment of the invention, the server 120 may include a sorting module 240 that enables sorting of the data, including the merged data. According to one embodiment of the invention, the sorting module 240 may sort the data based on various sorting criteria, including the chronology of data receipt, the type of device that originated the data, the type of technology used to obtain the data (e.g. CT, MRI, sonogram, etc.), the type of institution in which a data was obtained, the type of professional that obtained the data (i.e., radiologist, technologist, etc.), the user that is associated with the data, the patient that is associated with the data, demographic information, patient population information, the workflow sequence in which the data was captured, the severity of exam results, and/or other sorting criteria. According to one embodiment of the invention, the sorted data may enable tracking, reconstruction, reporting and/or monitoring of actions that are performed during medical examinations. According to one embodiment of the invention, the criteria associated with medical examinations may be used by the program to calculate QA scorecard metrics.

According to one embodiment of the invention, the server 120 may include a communications module 230 that communicates with the client computer 101, imaging devices 210 and/or databases to obtain information regarding the status of the imaging study along a defined workflow sequence. According to one embodiment of the invention, a defined workflow sequence includes various operations, such as image exam ordering, image exam scheduling, image exam acquisition, image processing, image archiving, image navigation, image interpretation, image exam reporting, image exam communication, and/or image exam billing. According to one embodiment of the invention, the communications module 230 provides the status of the imaging study workflow sequence including identifying the current user that is responsible for the image study, a completion percentage of the current stage of the imaging study, and/or other status information. According to one embodiment of the invention, the status of the imaging study workflow may be communicated to users in real-time and/or stored. According to one embodiment of the invention, parameters may be derived from the status of the imaging study workflow sequence to generate a QA scorecard for the various users.

According to one embodiment of the invention, the server 120 may include a report generating module 238 that generates reports based on the occurrence of pre-defined events, including a periodic query of the status of the imaging study, a interpretation that is forwarded by the radiologist, a clinical finding that is submitted by the clinician, and/or the occurrence of other pre-defined events.

According to one embodiment of the invention, the server 120 may include a billing module 242. According to one embodiment, the billing module 242 performs billing functions following completion of the reporting/communication process. The billing module 242 may analyze metrics to assess operational efficiency and accuracy of charges billed and to calculate any additional expenses that occur due to limitations in reporting by users, such as radiologists. According to one embodiment, the additional expenses may take a number of forms and may result from uncertainty and equivocation within the radiology report or radiologist recommendations for additional imaging exams, consultations, and procedures (e.g. biopsy). The billing module 242 may correlate imaging costs with quality of service deliverables, such as diagnostic accuracy and clinical outcomes.

According to one embodiment of the invention, the server 120 may include a scheduling module 244 that enables electronic scheduling, including image exam scheduling. According to one embodiment, the scheduling module 244 may include bi-directional electronic scheduling that provides real-time tracking features to update parties of scheduling changes. The scheduling module 244 may communicate with the communication module 230 and/or notification module 236, among other modules, to communicate the status of an appointment to users in real-time and/or stored.

According to one embodiment of the invention, the server 120 may include a notification module 236 that generates notifications and/or alerts based on the completion of reports, scheduling or the occurrence of predefined events. The notifications may be triggered by the release of items, such as status information, completion of an imaging report, change of an appointment, and/or other items. The notification module 236 may include monitoring features and/or confirmation features that track and record events, including the date and time that a notification is sent, the date and time that a notification is delivered, the date and time that a notification is opened, such as by return of an acknowledge receipt message, among other events. According to one embodiment, the notification module 236 may generate and forward notifications and/or alerts to client computers 101 and/or mobile devices, using known communication techniques including electronic mail messages, voice messages, telephone messages, text messages, instant messages, facsimile, and/or other communication techniques.

According to one embodiment of the invention, variables that are determined to have a deficiency during the imaging study process and that exceed a pre-determined QA standard threshold may trigger the computer program 110 to produce a notification and/or alert through the notification module 236 that may be instantaneously sent to users, via one or more communications techniques, alerting users as to the specific type of deficiency and requirement for correction.

According to one embodiment of the invention, a minimal amount of the data that is processed at the servers 120 may be stored in storage device 260 by the program 110. In other words, the servers 120 may perform data gathering and/or document generating functions and may thereafter purge all or portions of the retrieved data according to specified criteria. As a result, according to one embodiment, the program 110 may minimize security risks associated with exposing any confidential medical records to unauthorized parties at the servers 120. According to another embodiment of the invention, the retrieved data may be stored at the servers 120 by a program 110 for a predetermined amount of time before being purged. According to yet another embodiment of the invention, public record information, non-confidential retrieved data, and/or tracking information, such as client computer log files and/or image device log files may be stored in storage device 260 by the program 110.

According to one embodiment of the invention, the metrics module 232 may receive objective scores, such as a Likert scale of 1-4, to quantify user performance. For example, a score of 1 may be considered "non-diagnostic". This means little or no clinically useful (diagnostic) information is contained within the image study. Since the available information obtained during the examination of the patient does not answer the primary clinical question (i.e., indication for the study), then by definition this requires that the imaging exam be repeated for appropriate diagnosis.

A score of 2 may be considered "limited". This means that the information obtained during the image study is less than expected for a typical examination of this type. However, the information contained within the image study is sufficient to answer the primary clinical question. A requirement that this exam be repeated is not absolute, but is preferred, in order to garner maximal diagnostic value.

A score of 3 may be considered "diagnostic". This means that the information obtained during the image study is representative of the broad spectrum of comparable images, allowing for the patient's clinical status and compliance. Both the primary clinical question posed, as well as ancillary information, can be garnered from the image for appropriate diagnosis.

A score of 4 may be considered "exemplary". This means that the information obtained during the image study and overall image quality serves as an example that should be emulated as the "ideal" for that specific imaging study and patient population.

According to one embodiment of the invention, the data that is collected during the imaging study may analyzed by a metrics module 232 for performing prospective and retrospective trending analysis. The prospective and retrospective trending analysis enables automatic detection of immediate and recurrent problems, as they relate to equipment, personnel, data input, and overall workflow. The result of this automated technical QA analysis is that an automated and normalized analysis may be performed that minimizes subjectivity and human bias, among providing other benefits.

According to one embodiment of the invention, the metrics module 232 may automatically tally and record QA scores in a selected database. The QA scores may be cross-referenced by the computer program 110 to a number of independent variables including a technologist identifier, imaging modality, exam type, patient demographics, patient characteristics, patient body habitus, exposure parameters, image processing, exam location, equipment, day/time of exam for trending analysis, radiologist identification, referring clinician, clinical indication, among other variables. According to one embodiment, QA metrics may be determined based on multiple parameters, including the imaging modality, the clinical indication, the patient body habitus, prior surgery or history of trauma extraneous artifacts, contrast agents utilized, among other parameters. According to one embodiment, the QA metrics may be stored in imaging databases and may be searchable to serve as an educational resource for technologists in the discrimination of image quality.

According to one embodiment, the QA scorecard program 110 may include an automated QA analyzer for digital radiography that automates the image review process based at least on variables including motion, positioning, exposure, artifacts, collimation, and identifying data. The QA scorecard program 110 may provide recommendations on radiation dose optimization, store results in a searchable QA database, and provide objective feedback for technologist education and training.

According to one embodiment of the invention, the report generating module 238 may access the QA scores to display results from the metrics module 232. The reports may be accesses at any time by users, including the clinician, the radiologist, the technologist, and/or the department/hospital administrator to review individual and collective performance results. The trending analysis provided by this data can in turn be used for educational purposes, performance review, and new technology deployment.

According to one embodiment, the metrics module 232 analyzes data that is associated with a defined list of quality assurance (QA) benchmarks to objectively evaluate technologists, quantity a relative success of image acquisition and image processing and provide educational (data-driven) feedback in order to optimize technologist performance, among other benefits. The QA metrics may be tied to economic incentives, such as a pay for performance (P4P) systems, to create financial rewards for those technologists that provide high levels of quality-oriented service deliverables.

According to one embodiment, a quantifiable list of predefined technologist performance parameters which are defined by the computer program 110 may be used to measure overall performance of the technologist such as education, training, and certification; image quality scores; patient safety; dose reduction; data input, documentation, and verification; adherence to imaging and institutional protocols; trending analysis from QA database; image processing, among other parameters by the program 110.

According to one embodiment of the invention, the predefined parameters (see Table below) may be used to calculate an individual technologist QA score. The QA score, could be used as a multiplier for technical reimbursement or salary. According to one embodiment of the invention, higher priority variables, such as patient safety, may provide the highest multipliers, when compared with lower priority variables, such as adherence to protocols or image processing. According to one embodiment of the invention, each variable may be assigned a scoring scale of 1-10. According to one embodiment of the invention, the QA score may provide a method to standardize and track technologist QA profiles on local, national, and international levels.

TABLE

| Quantifiable Parameter | Scoring System | Source of Data |
| --- | --- | --- |
| Education, Training, and Certification | −3 - - - +3 | Departmental Records |
| Image Quality Scoring | −5 - - - +5 | QA Database |
| Patient Safety | −10 - - - +10 | RIS, EMR, PACS |
| Dose Optimization | −5 - - - +5 | RIS |
| Data Input and Documentation | −2 - - - +2 | PACS, RIS, EMR |
| Adherence to Protocols | −1 - - - +1 | HIS, RIS |
| QA Trending Analysis | −3 - - - +3 | QA Database |
| Image Processing | −1 - - - +1 | PACS |

According to one embodiment of the invention, the adherence to protocol parameter, such as an imaging protocol and/or an institutional protocol, may be defined by the computer program 110 to include, for example, time from receipt of exam acquisition request to completing acquisition; time from image exam completion to storage in an information source; technologist time reviewing imaging data; technologist time components for individual imaging acquisition segments; method of communicating results to a specialist; completeness of image acquisition data; patient safety profile, such as exposure levels of ionizing radiation or contrast administration; timeliness, including time to initiate image acquisition; feedback provided to the patient and specialists, such as the radiologist; participation in data collection; education and training, including imaging services and new technologies; reviews, including discretionary assessment of performance as it relates to imaging services; among other parameters. According to one embodiment of the invention, technologist performance metrics may be calculated from these parameters by the program 110.

According to one embodiment of the invention, the communication module 230 may access a number of informational sources, including the electronic medical record (EMR); the computerized physician order entry system (CPOE); the hospital information systems (HIS) 10, the radiology information systems 20 (RIS); the picture archival and communication system (PACS) 30; subjective feedback from the radiologist, patient, and clinicians; and/or other informational sources, to obtain technologist performance parameters. According to one embodiment, standard tags may be created within the various informational sources to identify individual QA data parameters.

Figure 3A:
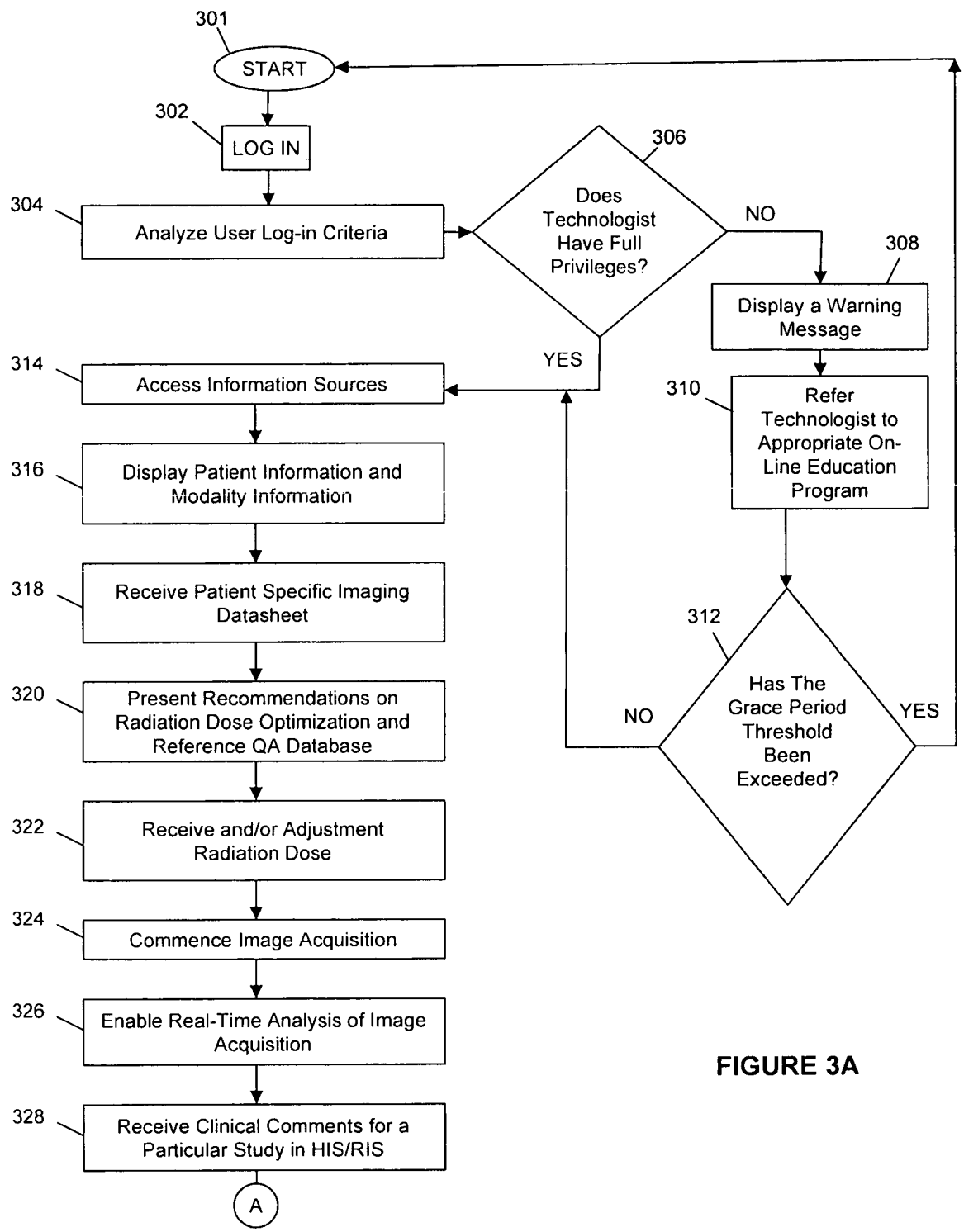
FIGS. 3A and 3B illustrate a flow chart of a workflow sequence quality assurance program for image acquisition and processing from the perspective of a technologist, according to one embodiment of the present invention.
Figure 3B:
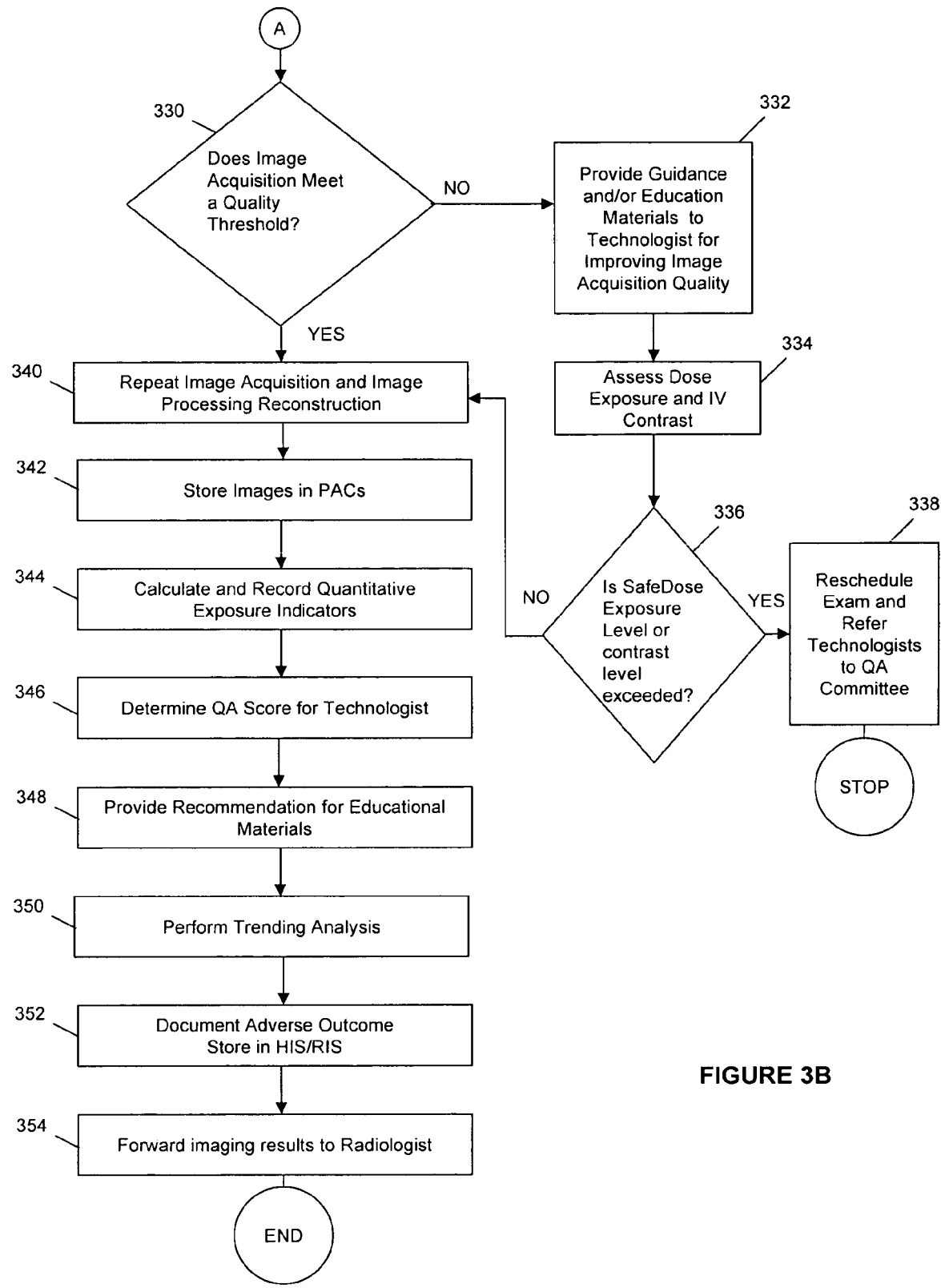

According to one embodiment of the invention illustrated in FIG. 3, the QA scorecard program 110 presents a welcome screen in operation, or step, 301. In operation 302, the QA scorecard program 110 displays a log-in screen and receives log-in criteria, such as a username and password. In operation 304, the QA scorecard program 110 analyzes the user log-in criteria against pre-stored log-in criteria for authorized users to determine if the user may gain access to the system. If the user log-in criteria is not approved, then the QA scorecard program 110 may notify the user of the registration failure and may return to the main log-in screen. If the user log-in criteria is approved, then in operation 306 the QA scorecard program 110 determines whether or not the user is assigned full privileges to perform actions within the QA scorecard program 110. If the user has full privileges, then the QA scorecard program 110 enables the technologist to access a personalized QA folder in operation 314.

According to one embodiment of the invention, if the user does not have full privileges, then in operation 308, the QA scorecard program 110 displays a warning message on the user interface advising the user that less than full privileges are associated with the log-in criteria. According to one embodiment of the invention, the warning message also may identify a grace period that is granted for regaining full privileges before all privileges are revoked. According to one embodiment of the invention, the grace period may be defined by a threshold, such as a number of log-ins, a number of days, or other threshold that may not be exceeded before all privileges are revoked.

According to one embodiment of the invention, a reduction of privileges may be prescribed by the program 110 for various predefined reasons, including failure to follow a predefined protocol, subjecting a patient to excess radiation, and/or failure to complete education program, among other predefined reasons. If the QA scorecard program 110 alerts the user to a reduction in privileges, then in operation 310 the QA scorecard program 110 may identify and recommend re-credentialing programs, including approved courses, computer training, or other re-credentialing programs. The QA scorecard program 110 will enable the user to immediately access the recommended re-credentialing programs through the QA scorecard program 110. According to one embodiment, the user may defer starting the recommended re-credentialing programs until a future date. After users successfully complete the re-credentialing program, the QA scorecard program 110 may restore full privileges to the user.

According to one embodiment of the invention, policies governing removal and re-institution of imaging privileges may be under the jurisdiction of a multi-disciplinary QA team including radiologists, administrators, and chief technologists, who would all have input into the overall process of reviewing data from the CPOE system.

According to one embodiment of the invention, the grace period threshold may be determined based on factors, such as the frequency of occurrence of one of predefined triggers, the severity of a technologist error, the amount of time required to complete a re-credentialing program, and/or other factors. In operation 312, the QA scorecard program 110 determines if the user has exceeded the allowed number of grace period log-ins. If the number of allowed grace period log-ins are exceeded, then the QA scorecard program 110 may revoke all privileges and the user may be presented with an alert that all privileges are revoked. The QA scorecard program 110 may prevent the user from proceeding further in the QA scorecard program 110 and the QA scorecard program 110 may return to the welcome screen. The QA scorecard program 110 may provide the user with contact information for re-establishing privileges.

If the grace period threshold has not been exceeded then, in operation 314, the QA scorecard program 110 may access one or more information sources, including the electronic medical record (EMR), the hospital information system 10 (HIS), the radiology information system 20 (RIS), the PACS 30, and/or an imaging QA data, among other information sources, to obtain information and/or records associated with the selected patient. According to one embodiment of the invention, a standard tag may be created by the program 10 within the various informational sources to identify individual QA data parameters.

According to one embodiment of the invention, the program 110 may automatically record imaging data in the imaging QA database may automatically record and archive data that is produced during each imaging exam. According to one embodiment of the invention, the QA scorecard program 10 periodically tracks and analyzes the QA database based on a number of predetermined parameters including the modality, acquisition location, performing technologist, exam date and time, anatomic region, radiation exposure parameters, study indication, pertinent patient clinical and demographic information (including body habitus), number of images obtained, number of images rejected, patient motion, artifacts, positioning limitations, contrast parameters, image processing, technologist perceived image quality score, radiologist perceived image quality score, reject analysis code, among other parameters.

In operation 316, the QA scorecard program 110 may display patient information, modality information, and/or other information or records that are associated with the selected patient. According to one embodiment of the invention, the technologist may review the data elements that are entered into the CPOE system before the requested imaging exam is performed. The availability of the data elements provides an opportunity for the technologist and/or radiologist to clarify any discrepancies or clinical questions. The QA scorecard program 110 enables the technologist and/or radiologist to make adjustment to the exam protocol and/or to optimize the image exam prior to performing the image exam. According to one embodiment of the invention, discrepancies are defined to include data that is inconsistent with other information that is included in the record. For example, the clinician may input data indicating that no prior history of cancer exists. However, a prior imaging report may show past medical history of cancer.

According to one embodiment of the invention, the QA scorecard program 110 may display an imaging data sheet that is customized by a user for the patient. According to one embodiment of the invention, the imaging data sheet provides users with important aspects of the patients medical history. The imaging data sheet may have a standard format and may include data, such as past medical and surgical history; prior imaging exams and results, including those performed at outside facilities; current clinical problems; pertinent findings on physical exam; pertinent laboratory and/or pathology data; ancillary data, including procedural findings (e.g. colonoscopy, bronchoscopy), operative or consultation notes, clinical testing (e.g., EEG, EKG); technical information related to the imaging exam performed; technologist observations, including pertinent findings and measurements; technologist notes, including complications, exam limitations; among other data.

According to one embodiment, the QA scorecard program 110 enables creation of a universal, patient-specific imaging data sheet for digital images. According to one embodiment, the imaging data sheet may be stored in the EMR, RIS, and/or PACS, among other information systems. According to one embodiment of the invention, when a new entry or modification is made to the imaging data sheet, a time-stamp data may be included in the record, along with the identification of the person inputting (or modifying) the data. According to one embodiment, the time-stamped data may provide objective data analysis. Imaging departments are able to record individual time-stamped data throughout the course of the imaging cycle, from the time an imaging study is electronically completed to the time the imaging study is forwarded and reviewed.

According to one embodiment of the invention, each user may create profiles for the imaging data sheet and may customize the imaging data sheet display to their own individual preferences. According to one embodiment of the invention, the customized imaging data sheet may be linked to users via a log-in criteria.

According to one embodiment of the invention, new data may be input into the imaging data sheet via the QA scorecard program 110 by clinicians, nurses, radiologist, technologist or other authorized users. For example, the technologist may enter data based on discussions with the patient and/or based on retrieval of relevant data from an information source. Technologist are typically the eyes and ears of the interpreting physician. Generally, radiologists do not have direct contact with the patient. Clinical questions pertaining to the medical imaging study being performed, such as clinical indication, contraindications to contrast or specific types of imaging procedures, past medical and surgical history, previous outside imaging studies and findings, additional tests performed, and current medical treatment, among other clinical questions, are often requested by technologist and recorded by the program 110 into imaging folder along with the imaging study. Additional data recorded by the technologist would include any adverse outcomes experienced, such as contrast allergic reaction or extravasation; technical limitations; communication directives, including holding patient pending stat communication of results to the physician; and/or other adverse outcomes. The imaging data sheet provides valuable information to the interpreting radiologist and become a vital part of the patient's imaging and medical record. By documenting this information, current and future imaging and patient outcomes may be optimized in the form of improved image exam selection and protocol selection, reduction of contrast reactions, and improved interpretation accuracy, among other benefits.

According to one embodiment of the invention, new data may be input into the imaging datasheet via the QA scorecard program 110 through computer-derived entry using natural language processing (NLP). According to one embodiment of the invention, the imaging data sheet may have separate tabs for each individual imaging modality, and may include technical data, measurements, and technologist notes specific to each individual exam/modality. In operation 318, the QA scorecard program 110 receives and stores the patient specific imaging data sheet.

In operation 320, the QA scorecard program 110 may reference the QA database and present recommendations for radiation dose optimizations. In operation 322, the QA scorecard program 110 receives and/or enables adjustment of the radiation dose levels. According to one embodiment of the invention, the QA scorecard program 110 may electronically track, store, and analyze entries from the technologist to create technologist profiles on entry habits, completeness of input data, and compliance with protocols, among other elements. This profile data may in turn be used for technologist education and training.

According to one embodiment of the invention, electronic communication pathways may be provided by the program 110 to automate the communication between the technologist and others, including clinicians, radiologists, supervisors, and/or others. Communication preferences may be defined through user profiles and may include text messaging, e-mail alerts, cell phone, faxing, and/or other communication methods.

In operation 324, the QA scorecard program 10 may signal that the imaging acquisition may commence and may allow the technologist to perform the imaging study. During the imaging study, the QA scorecard program 110 may evaluate adherence to protocols. The QA scorecard program 110 may track protocols the imaging department and institution to determine adherence with patient safety, privacy and confidentiality, among other factors that may contribute to clinical outcomes. According to one embodiment of the invention, the QA scorecard program 110 may electronically document compliance with pre-defined protocols.

In operation 326, the QA scorecard program 110 enables real-time analysis of image acquisition. According to one embodiment of the invention, the technologist may make adjustments to parameters exposure settings, patient positions, and other parameters during the imaging study. According to one embodiment of the invention, the QA scorecard program 110 may apply predefined formulas to perform imaging processing and/or reconstruction of the acquired images based on specific modalities and types of imaging exams. The imaging processing and/or reconstruction may be performed by the program 110 to enhance image quality and disease detection. According to one embodiment of the invention, imaging processing and/or reconstruction may also be performed manually based on specialized expertise and training of the technologist. According to one embodiment of the invention, the metrics module 232 may quantify and resources expended by the technologist to apply these advanced image processing techniques.

According to one embodiment of the invention, the QA scorecard program 110 may present the technologist with support tools. The QA scorecard program 110 may present decision support tools, including computer-aided detection (CAD), specialized image processing, electronic teaching files and other on-line educational resources for patient management, such as the National Library of Medicine (NLM) for literature searches.

In operation 328, the QA scorecard program 110 receives clinical comments from the technologist regarding several factors, including deficiencies; quality of exam; contrast injections, including rate of extravasation, amount of contrast injected; informed consent, including whether consent was obtained and the level of consent completeness; documentation of contraindications, allergies, and adverse actions, including whether these occurred and are documented; any physical injury that occurred during imaging exam; patient education; radiation exposure, including reject/retake analysis, collimation, exposure parameters; whether radiation doses were adjusted; documentation of technical and clinical data; and/or other factors. According to one embodiment of the invention, the metrics module 232 may generate a QA score for the technologist based on these factors.

In operation 330, the QA scorecard program 110 determines whether the image acquisition meets a pre-defined quality threshold. If the image acquisition does not meet the pre-defined quality threshold, then in operation 332 the QA scorecard program 110 provides guidance and/or education materials to the technologist for improving image acquisition quality. In operation 334, the QA scorecard program 110 assesses dose exposure and/or IV contrast. In operation 336, the QA scorecard program 110 determines whether a safe dose level or IV contrast level is exceeded. If a safe dose level, IV contrast level, and/or other patient safety factor(s) is exceeded, then in operation 338 the imaging study is re-scheduled by the program 110 and the technologist is referred by the program 110 to a QA committee and the image acquisition is stopped.

External review serves as a mechanism for each technologist to be evaluated both prospectively and retrospectively by their medical personnel. According to one embodiment, prospective evaluation may be provided by radiologists that serve as imaging consultants and provide feedback as to the imaging exam acquisition. By random electronic auditing of imaging studies by the program 110, review can be directly incorporated into patient management and provide an important subjective tool for providing feedback to the technologist on imaging service. The data derived from this review may be entered into a comprehensive QA database by the program 110 and provided to the technologist by the program 110 on a periodic basis for educational purposes.

If a safe dose level or IV contrast level is not exceeded as determined by the program 110 in a check against predetermined parameters, then in operation 340, the QA scorecard program 110 instructs the technologist to repeat the image acquisition and enables image processing reconstruction. According to one embodiment of the invention, if the dose level and/or IV contrast level are low below predetermined parameters, then the image acquisition protocol may be repeated by the program 110 without adjustments. According to one embodiment of the invention, if the dose level and/or IV contrast level are borderline, then the image acquisition protocol may be adjusted by program 110 to include lower radiation levels and/or a reduced IV contrast. In operation 342, the acquired images are stored in PACS 30 and/or other database.

In operation 344, the QA scorecard program 110 may calculate and store quantitative exposure indicators. According to one embodiment of the invention, the quantitative exposure indicators and other data may be obtained from the image DICOM header files. Alternatively, the QA scorecard program 110 may calculate the ionizing radiation that is associated with each individual medical imaging exam, based on acquisition and exposure parameters. The calculation may be performed prospectively and may be stored by the program 10 to track longitudinal radiation dose and carcinogenesis risk. According to one embodiment, HIS 10 and RIS 20, and/or other information sources, may be updated by the program 110 to include the calculated safety factors.

According to one embodiment, in order to optimize safety concerns and record/track cumulative data, the QA scorecard program 110 provides patient safety data at any location where the patient is seeking and/or receiving medical imaging services. In the event that the patient had a previous allergic reaction to contrast at another medical imaging facility and the patient now presents with altered mental status and cannot provide accurate historical data, the QA scorecard program 110 provides access to the pre-existing safety data before any imaging exam is performed. By storing the QA Scorecard data within a universal EMR, this data is made accessible to appropriate healthcare providers at any location so that appropriate action can be taken.

One method of providing universal accessibility for the data is to use extensible mark-up language (XML). XML further enables communication between disparate information technologies by allowing creation of a standard tag for individual QA data parameters. According to one embodiment, QA metrics may be employed to define XML tags, such as examination time, technologist retake, reject analysis, among other QA metrics. According to one embodiment, XML tags may be communicated among information technologies, such as modalities, information systems, PACS, EMR, CPOE. According to one embodiment, XML tags may be automatically downloaded into a universal QA database.

According to one embodiment of the invention, the QA scorecard program 110 may correlate radiation dose and image quality and may apply an algorithm to minimize exposure and optimize quality. According to one embodiment of the invention, the QA scorecard program 110 may store the results in the QA database. According to one embodiment of the invention, cumulative radiation exposure levels may be automatically calculated and correlated with image quality scores to provide technologists with objective feedback for improving quality and safety. According to one embodiment of the invention, correlating exposure levels and image quality provides reproducible and objective feedback to technologists.

In operation 346, the metrics module 232 may generate a QA score for the technologist based on several factors, including radiation exposure, including reject/retake analysis, collimation, exposure parameters; deficiencies; contrast injections, including rate of extravasation, amount of contrast injected; informed consent, including whether consent was obtained and the level of consent completeness; documentation of contraindications, allergies, and adverse actions, including whether these occurred and are documented; any physical injury that occurred during imaging exam; patient education, whether radiation doses were adjusted; documentation of technical and clinical data; and/or other factors.

According to one embodiment, the QA scorecard program 110 may present the technologist with access to individual QA folders for review their QA scores. The QA folders provide valuable educational resources for technologists to obtain subjective feedback from radiologists and/or supervisory technologists regarding overall image quality, positioning, and exposure parameters. Technologists may review their individual QA folders on a regular basis to review comments and critiques made to their submitted exams, along with a review of outliers, such as low quality QA scores. Reviewing QA folder allow technologists to obtain feedback as to specific types of studies or patients that present greater difficulty and serve as a source for improvement. According to one embodiment, the QA folders and corresponding images may includes dates, times, and exams electronically recorded for documentation purposes and for review by administrative and supervisory staff. A technologist that frequently reviews and learns from information contained within the QA database should demonstrate improvement in quality performance, as evidenced by upward trending in overall and specific image quality scores. This can serve as a quantitative means for the program 110 to track technologist performance and provide incentives for improvement of QA scores, both on an individual technologist and departmental level.

In operation 348, the QA scorecard program 110 may provide recommendations to the technologist for education and training. Technologists that improve their educational skill set through continuing medical education and advanced certification may increase QA scores. These educational programs may be automated and customized to a specific problem, such as the program 110 bookmarking certain on-line education materials to specific imaging data. For example, maybe a website has an overview on particular imaging devices. If a technologist is inappropriately setting exposure levels, the program 110 may identify the error and direct the technologist to the on-line educational program that best fits the area of concern. According to one embodiment, technologists may receive subspecialty certifications based on documented proficiencies such as work experience, testing, and CME credits. Once the educational program has been completed, the QA scorecard program 110 may increase QA scores.

In operation 350, the QA scorecard program 110 may perform trending analysis. According to one embodiment, trending analysis may be performed to demonstrate outliers. According to one embodiment, QA scores may be plotted over time, to identify how ongoing education and training efforts are translating into quality improvement. According to one embodiment, data may be fractionated to investigate trending for different variables, such as the interpreting radiologist, type of exam, specific views within an exam, patient profile, technology utilized, clinical indication, and day/time of exam performance. This may provide the technologist and supervisory staff with information for improving workflow and scheduling, technology purchases and room assignments, processing parameters used for specific types of patients and exam indicators, and subjective preferences of interpreting radiologists and clinicians.

According to one embodiment, the QA scorecard program 110 may track, record and analyze longitudinal patient-specific safety data and technologist-specific safety data, both on an individual patient and group basis. This provides insight as to whether individual technologist are regularly over-exposing and may provide educational feedback to specific technologists. Additionally, mandatory educational resources may be forwarded to targeted technologists. This "technologist safety profile" data and trending analyses may be correlated with local, regional, and national norms, with data available to third party payers and insurers to assist with economic incentive programs (P4P) to encourage improved performance and continuing medical education, as it relates to medical imaging safety factors.

In operation 352, the QA scorecard program 110 may store any adverse outcomes from the imaging study in a patient's profile. According to one embodiment, the adverse outcomes may be stored in the HIS 10, the RIS 20, the EMR, and/or other information source.

In operation 354, the QA scorecard program 110 may forward the imaging results to the radiologist, clinician or other users. Communication protocols may be provided to ensure that the information contained within the medical imaging study is provided to the radiologist in a timely fashion and appropriately utilized for clinical management. The QA scorecard program 110 may alert the radiologist when the technologist has completed the image acquisition.

The QA scorecard program 110 may present images to the radiologist through information sources, such as PACS 30, among other information sources. The QA scorecard program 110 may alert users if the imaging study contains unexpected results or emergent findings. If the imaging study does not include unexpected results or emergent findings, then the radiologist may be presented with the images pursuant to a standard protocol. Alternatively, if the imaging study includes unexpected results or emergent findings, then the radiologist may be presented with the results pursuant to a special protocol.

When the QA scorecard program 110 receives information of clinically unexpected or emergent findings during the course of imaging acquisition, the QA scoreboard program 110 may generate an alert that notifies the ordering clinician, radiologist, a supervisor or other user to immediately contact the technologist to directly receive these emergent findings.

When the imaging study includes unexpected results or emergent findings, the scorecard program 110 may send an alert to the appropriate users. Whether the communication occurs electronically or verbally, the QA scorecard program 110 documents the communication by time stamping and storing the communication for future analysis. Upon receipt of the alert, the radiologist may immediately contacts the imaging department staff (i.e., technologists, administrators) to discuss the clinical concerns. The QA scorecard program 110 documents the communication between the technologist and appropriate users by time stamping and storing the communication for future analysis.

According to one embodiment of the invention, QA scorecard parameters for reporting and communication by the program 110 may include criteria such as, time from exam acquisition completion to receipt by radiologist; time from receipt by radiologist to actual review; specific components of the report reviewed by the radiologist time reviewing imaging data, such as image open time and close time; imaging links, including complete imaging file, key images, snapshot; ancillary data, including teaching files, NLM, review articles; communication; method of communication; acknowledgement of receipt of communication; bi-directional consultation; time to initiate treatment; tracking of follow-up recommendations; subjective value; among other criteria.

The QA scorecard program 110 may calculate metrics from various parameters. According to one embodiment, the QA database and time-stamped data elements within the QA database enable the various time requirements to be quantified for various components within the overall imaging/treatment cycle. By doing so, an objective methodology is provided to assess radiologist availability and responsiveness with regards to imaging examination data. This time-stamped data becomes a valuable tool for users, such as administrators, radiologists and clinicians, to assess overall workflow and identify bottlenecks and limitations within the system. The QA database also provides valuable data to the community at large as to the time efficiency of imaging service and clinical providers.

According to one embodiment, combined subjective and objective feedback is important to provide data to technologists as to how their performance is perceived by imaging service providers, such as radiologists, and customers, such as patients.

According to one embodiment of the invention, the technologists may also obtain feedback from the patient via electronic and/or paper surveys. The feedback may include the patient's subjective perceptions as to a number of factors, including conscientiousness, education, responsiveness to questions, communication skills and/or timeliness, among other factors. The feedback may be obtained from the patient before the patient leaves the imaging department or later via electronic or conventional mail. Questions may be posed using a Likert scale to provide a quantitative value. Because answers may be biased (some people grade too harshly, others too easily), the scored answers may be extrapolated by the program 110 based on individual biases relative to the larger group. Subjective answers may be reviewed by an impartial administrator who records information into the QA database to identify consistent trends.

Active participation in prospective data collection and analysis is a component of the QA Scorecard and pay for performance system. The data that is collected and analyzed by the program provides the foundation for evaluating reports, diagnostic accuracy, and clinical outcomes analysis.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. An apparatus for generating a quality assurance scorecard, comprising:
   at least one client computer;
   a server comprising:
      a merging module which receives data from all devices networked to said server, including at least one of said client computer, an imaging device, and/or databases, said merging module which stores said received data in a storage device;
      a sorting module which enables sorting of at least said merged data, wherein said sorting module sorts said data based on predetermined sorting criteria;
      wherein said sorted data enables tracking, reconstruction, reporting and/or monitoring of actions performed during an imaging examination;
      a metrics module which analyzes said data collected during said imaging examination, and performs prospective and retrospective trending analysis, said trending analysis which enables automatic detection of immediate and recurrent problems in said imaging examination, and automatically tallies and records quality assurance scores in a selected database; and
      an automated quality assurance analyzer for digital radiography which automates an image review process to track and analyze factors based on patient motion, patient positioning, imaging artifacts, collimation, and patient identifying data, in order to optimize the quality of said imaging examination.

2. The apparatus according to claim 1, wherein said quality assurance scores are cross-referenced to a number of independent variables including at least one of a technologist identifier, imaging modality, examination type, patient demographics, patient characteristics, patient body habitus, exposure parameters, image processing, examination location, equipment, day/time of exam for trending analysis, radiologist identification, referring clinician, and clinical indication.

3. The apparatus according to claim 1, wherein said metrics module compiles said quality assurance scores based on multiple parameters, including at least one of an imaging modality, clinical indication, patient body habitus, prior surgery or history of trauma extraneous artifacts, radiation dose, and contrast agents utilized.

4. The apparatus according to claim 3, further comprising:
   an imaging database which stores said data compiled by said metrics module.

5. The apparatus according to claim 4, wherein said automated quality assurance analyzer analyzes radiation exposure and calculates a recommended radiation dose.

6. The apparatus according to claim 3, wherein said quality assurance scores are calculated based on at least one of chronology of data receipt, type of device that originated said data, type of technology used to obtain said data, type of institution in which said data was obtained, type of professional that obtained said data, the user associated with said data, a patient associated with said data, demographic information, patient population information, workflow sequence in which said data was captured, and a severity of imaging examination results.

7. The apparatus according to claim 1, wherein said received data includes at least client computer audit log data and/or an image device audit log data.

8. The apparatus according to claim 1, further comprising:
   a communications module which communicates with said client computer, said imaging device and/or databases, to obtain information regarding a status of said imaging examination along a predetermined workflow sequence.

9. The apparatus according to claim 8, wherein said predetermined workflow sequence includes at least one of image examination ordering, image examination scheduling, image examination acquisition, image processing, image archiving, image navigation, image interpretation, image examination reporting, image examination communication, image examination billing; identification of a current user responsible for said image study, and a completion percentage of a current stage of said imaging study.

10. The apparatus according to claim 9, wherein said communications module provides said information in real-time.

11. The apparatus according to claim 10, further comprising:
    an authentication module which identifies users.

12. The apparatus according to claim 11, further comprising:
    a biometric apparatus which provides identification information to said authentication module.

13. The apparatus according to claim 1, further comprising:
    a report generating module which generates reports based on predetermined events, including at least one of a predetermined status of an imaging study, and/or a finding forwarded by a user.

14. The apparatus according to claim 1, further comprising:
    a notification module which generates notifications and/or alerts based on at least one of a completion of an imaging report, scheduling of examinations, and release of status information.

15. The apparatus according to claim 6, wherein said quality assurance scores are used to evaluate a technologist performance in at least one of education; training; certification; image quality scores; patient safety; radiation dose reduction; data input, documentation and verification; adherence to imaging and institutional protocols; trending analysis using quality assurance data; and image processing.

* * * * *